United States Patent [19]  
Tong

[11] Patent Number: 4,558,134  
[45] Date of Patent: Dec. 10, 1985

[54] CERTAIN PHENOXY-PYRIDINE-CARBONITRILES HAVING ANTIVIRAL ACTIVITY

[75] Inventor: Yulan C. Tong, Walnut Creek, Calif.

[73] Assignee: The Dow Chemical Company, Midland, Mich.

[21] Appl. No.: 455,439

[22] Filed: Jan. 3, 1983

[51] Int. Cl.[4] .................... C07D 213/57; A61K 31/44
[52] U.S. Cl. .................... 514/344; 546/288; 546/323
[58] Field of Search .......... 546/288; 514/344

[56] References Cited

U.S. PATENT DOCUMENTS

| | | | |
|---|---|---|---|
| 3,639,413 | 2/1972 | Domenico | 546/294 |
| 3,655,897 | 4/1972 | Witzel | 514/345 |
| 3,719,682 | 3/1973 | Domenico | 546/288 |
| 3,931,200 | 1/1976 | Gulbenk | 546/305 |
| 3,954,782 | 5/1976 | Fleckenstein et al. | 546/306 |
| 4,162,321 | 7/1979 | Wehinger et al. | 514/150 |
| 4,212,980 | 7/1980 | Butler | 546/288 |
| 4,229,457 | 10/1980 | Butler | 514/344 |
| 4,329,167 | 5/1982 | Rempfler et al. | 71/94 |

OTHER PUBLICATIONS

Blank et al., Journal of Medicinal Chemistry, vol. 20, (12) pp. 1572–1577, (1977).

*Primary Examiner*—Alan L. Rotman

[57] ABSTRACT

Substituted pyridines exhibiting antiviral activity are disclosed. Also disclosed are methods of use involving the substituted pyridines as well as compositions comprising a non-toxic, pharmaceutically-acceptable carrier in combination with one or more said substituted pyridines.

72 Claims, No Drawings

CERTAIN PHENOXY-PYRIDINE-CARBONITRILES HAVING ANTIVIRAL ACTIVITY

SUMMARY OF THE INVENTION

The present invention is directed to an antiviral compound of the formula:

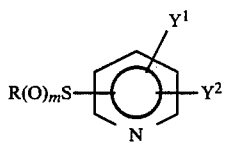
(I)

wherein $Y^1$ is cyano (—CN) or

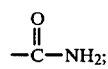

$Y^2$ is phenoxy; and, relative to the $R(O)_mS$— substituent, R is lower alkyl and m is the integer 0, 1, or 2 provided that the $Y^2$ substituent and the $R(O)_mS$— substituent are in para orientation with respect to one another.

As used herein, the term "phenoxy" refers to unsubstituted or substituted phenoxy radicals. The term "substituted phenoxy" refers to a phenoxy moiety optionally substituted with from 1 to 3 substituents selected from the group consisting of fluoro, chloro, bromo, or iodo; or to a phenoxy moiety mono-substituted with a benzoyl radical, i.e.,

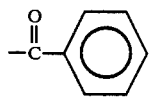

forming a benzoylphenoxy radical; and the term "lower alkyl" refers to aliphatic, straight or branched chain radicals of from one to six carbon atoms, both inclusive.

Those compounds of formula I which are preferred for antiviral use are those compounds wherein $Y^1$ is cyano, $Y^2$ is substituted phenoxy, and relative to the $R(O)_mS$— substituent R is lower alkyl and m is the integer 0, 1 or 2.

Of the preferred compounds, those compounds wherein $Y^1$ is cyano, $Y^2$ is a dichloro-substituted phenoxy moiety, and relative to the $R(O)_mS$— substituent R is lower alkyl of from one to four carbon atoms both inclusive and m is the integer 0, 1 or 2 are especially preferred.

Of the especially preferred compounds, those compounds wherein $Y^1$ is cyano, $Y^2$ is a dichloro-substituted phenoxy moiety, and relative to the $R(O)_mS$— substituent R is lower alkyl of from two to four carbon atoms both inclusive and m is the integer 0 are particularly preferred.

The compounds of the present invention exhibit antiviral activity. That is, the compounds disclosed herein can be used to inhibit viral replication by contacting the virus and/or a virus host cell containing said virus with an effective amount of one or more of the compounds disclosed by formula I. The present invention is further directed to methods of using the compounds of the invention as antiviral agents in which a virus or virus host cell (i.e., a cell susceptible to infection by the virus) is contacted with one or more of the subject compounds. The present invention is further directed to antiviral compositions which can contain from about 0.00001 percent by weight or less to about 99 percent by weight of one or more of the subject compound(s) in combination with a non-toxic, pharmaceutically-acceptable carrier. Typically, though not necessarily, in those combinations employing a low percentage of the subject compound(s), the pharmaceutically-acceptable carrier is in liquid form. Therefore, a composition containing from about 0.00001 percent or less by weight of the subject compound(s) is equivalent to a composition containing about 0.1 microgram (μg) or less of the subject compound(s) per milliliter (ml) of carrier.

DETAILED DESCRIPTION OF THE INVENTION

The compounds of the present invention may be conveniently prepared by one of the following methods. Typically, though not necessarily, the compounds are prepared via an intermediate of the formula:

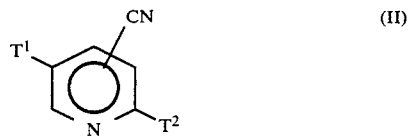
(II)

wherein $T^1$ is chloro when $T^2$ is RS; or $T^1$ is RS when $T^2$ is chloro. As used to define formula II and throughout the following description, R has the same meaning as defined for formula I.

The compounds of formula II are either commercially available or may be prepared from known compounds by well-known methodology or by techniques disclosed herein.

(a) Preparation of the substituted-2-pyridinecarbonitriles

The 6-phenoxy-3-(R-thio)-2-pyridinecarbonitriles and the 3-phenoxy-6-(R-thio)-2-pyridinecarbonitriles may be prepared in the following manner. 3,6-Dichloro-2-pyridinecarbonitrile is reacted with the desired alkylmercaptan (i.e., R-thiol where R is defined as for formula I) in an inert solvent such as tetrahydrofuran (THF) or dimethylsulfoxide (DMSO) in the presence of potassium t-butoxide (t-BuOK) or other strong base. The reaction may be carried out over a broad temperature range such as from about 0° C. to about 45° C. Typically, though not necessarily, the reaction yields the following mixture of isomers: 6-chloro-3-(R-thio)-2-pyridinecarbonitrile; 3-chloro-6-(R-thio)-2-pyridinecarbonitrile; and 3,6-bis-R-thio-2-pyridinecarbonitrile. Generally, 6-chloro-3-(R-thio)-2-pyridinecarbonitrile is the predominant isomer, however the relative ratio of isomers obtained is a function of the reaction conditions (i.e., duration of reaction, temperature, solvents, etc.) and/or the molar proportions of reactants used. The mixture of isomers is then separated by conventional techniques such as chromatographic separation. The desired isomer is then mixed with about an equimolar amount of an appropriate phenol or substituted phenol (i.e., a compound suitable for forming the $Y^2$ substituent of formula I) in a suitable inert organic solvent such as THF or DMSO in the presence of a base such as t-BuOK. This mixture is then heated at reflux temperature for a period of time sufficient to obtain the phenoxy-(R-thio)-2-pyridinecarbonitrile, which may then be conveniently oxidized to the corresponding R-sulfinyl or R-sulfonyl compounds (that is, those compounds of formula I in which m is the integer 1 or 2, respectively). Such oxidation procedures are well-known in the art and may be performed using oxidizing agents such as trifluoroacetic acid/hydrogen peroxide, m-chloroperbenzoic acid, DABCO® dibromide and the like. Hydrolysis of the 2-cyano group to the 2-carboxamide (i.e., where $Y^1$ is

in formula I) may also be achieved during the above-described oxidation by performing said oxidation under reaction conditions suitable for forming the 2-carboxamide.

By varying the oxidizing agent, the concentration and amount of oxidizing agent and reaction conditions, the oxidation reactions described herein may be modified to form a predominance of R-sulfinyl or R-sulfonyl compounds as well as 2-cyano or 2-carboxamide compounds. Such modifications are well within the purview of one skilled in the art.

(b) Preparation of the substituted 3-pyridinecarbonitriles

The substituted 3-pyridinecarbonitriles may be prepared by one of the following two methods.

(i) An appropriate phenol or substituted phenol (i.e., a compound suitable for forming the $Y^2$ substituent of formula I) is reacted with a molar excess of chloroacetaldehyde diethyl acetal (ClCH$_2$CH(OCH$_2$CH$_3$)$_2$) in the presence of potassium hydroxide to form a phenoxyacetaldehyde diethyl acetal. This procedure is taught by Lipinski et al., *J. Med. Chem.*, 23, 1026 (1980) which is incorporated herein by reference. The phenoxyacetaldehyde diethyl acetal is then added to a mixture containing POCl$_3$ and DMF and heated for a period of time sufficient to form 2-(phenoxy)-3-dimethylaminopropenal which is then reacted with malonamide (i.e., CH$_2$(CONH$_2$)$_2$) in the presence of t-BuOK and DMSO. The desired, 5-(phenoxy-2-hydroxy-3-pyridinecarboxamide may then be collected by conventional techniques. The isolated pyridinecarboxamide is then added to phenylphosphonic dichloride followed by the addition of PCl$_5$. The mixture is heated and the desired 5-(phenoxy)-2-chloro-3-pyridinecarbonitrile is isolated. This product may then be treated with the desired alkylmercaptan in NaOH to form the 5-(phenoxy)-2-(R-thio)-3-pyridinecarbonitrile which may then be oxidized to the R-sulfinyl or R-sulfonyl form and/or to the 3-pyridinecarboxamide compound if desired.

(ii) 2-Chloro-5-nitro-3-pyridinecarbonitrile (a compound well-known in the art; see *J. Am. Chem. Soc.*, 77:1045, 1955) is reacted with an appropriate phenol or substituted phenol (i.e., a compound suitable for forming the $Y^2$ substituent of formula I) to give the corresponding 2-phenoxy-5-nitro-3-pyridinecarbonitrile. This compound is then hydrogenated by an appropriate catalyst to the corresponding 5-amino compound which is subsequently diazotized by a known procedure. See *J. Org. Chemistry*, 44, 3080 (1979) which is incorporated herein by reference. The diazonium salt is then reacted with the desired alkylmercaptan in sodium hydroxide and acetonitrile under conditions such that 2-phenoxy-5-(R-thio)-3-pyridinecarbonitrile is obtained (where R has the same meaning as defined for formula I). Subsequent oxidation of this compound to the R-sulfinyl or R-sulfonyl form and/or to a 3-pyridinecarboxamide compound may be achieved by the procedures described herein.

(c) Preparation of the substituted 4-pyridine carbonitriles

In preparing the substituted 4-pyridinecarbonitriles, 2,5-dichloropyridine may be lithiated with lithium diisopropylamide by substantially the same procedure as described in *Tetrahedron Letters*, 21, 4137 (1980), (which is incorporated herein by reference) forming the 2,5-dichloro-4-pyridinecarboxaldehyde upon quenching with dimethylformamide (DMF). The aldehyde may then be reacted with hydroxylamine hydrochloride under reaction conditions such that 2,5-dichloro-4-pyridinecarboxaldehyde oxime is formed. The oxime may then be dehydrated to the corresponding nitrile by heating at reflux temperature in acetonitrile in the presence of phosphorus oxychloride. The 2,5-dichloro-4-pyridinecarbonitrile which is obtained is reacted with about an equimolar amount of the desired alkylmercaptan as described previously giving a mixture of isomers, the 2-chloro-5-(R-thio)-4-pyridinecarbonitrile and the 5-chloro-2-(R-thio)-4-pyridinecarbonitrile (where R has the same meaning as defined for formula I). The mixture of isomers is then separated by conventional techniques such as described herein. The desired derivative is then reacted with an appropriate phenol or substituted phenol (i.e., a compound suitable for forming the $Y^2$ substituent of formula I) following substantially the same procedure as described above. The R-thio substituent may be oxidized to the R-sulfinyl or R-sulfonyl form as previously described. Similarly, oxidation under appropriate conditions may form the substituted-4-pyridinecarboxamide from the corresponding substituted-4-pyridinecarbonitrile.

The above-described procedure may be modified by carrying out the alkylmercaptan substitution first, followed by lithiation, quenching with DMF and then reaction with hydroxylamine hydrochloride to form the 5-chloro-2-(R-thio)-4-pyridinecarboxaldehyde oxime. As described, subsequent dehydration of the oxime gives the desired 4-pyridinecarbonitrile which may then be reacted with a phenol or substituted phenol (i.e., a compound suitable for forming the $Y^2$ substituent of formula I) followed by the described oxidation(s), if desired.

The various compounds described herein are recovered and purified using procedures well known in the art. Recovery procedures include, for example, dilution of the reaction mixture with water, filtration, decantation, centrifugation and extraction with appropriate solvents. Purification procedures include, for example, various chromatographic techniques, distillation (often at reduced pressure), washing and recrystallization.

The following examples are provided as a means of illustrating the present invention and are not to be construed as a limitation thereon.

EXAMPLE 1

Preparation of
6-chloro-3-methylthio-2-pyridinecarbonitrile and
3-chloro-6-methylthio-2-pyridinecarbonitrile 69.2 Grams (g) of 3,6-dichloro-2-pyridinecarbonitrile was dissolved in 250 milliliters (ml) of THF and chilled to about 10° C. Methanethiol (19.2 g) was added and the whole mixture was cooled to about 5° C. While the temperature was maintained at about 0° to 5° C., 44.9 g of t-BuOK in 550 ml of THF was added slowly. After the addition of t-BuOK was complete, the reaction mixture was allowed to warm to room temperature, and was stirred for 3 hours and then poured onto ice, forming a precipitate which was collected by filtration. The precipitate was dissolved in $CH_2Cl_2$, dried, concentrated and diluted with hexane to give 24.7 g of white crystalline material which was subsequently identified by NMR to be 6-chloro-3-methylthio-2-pyridinecarbonitrile. The filtrate from the above-described filtration was then concentrated leaving a solid which was recrystallized twice and filtered (retaining the filtrates after each recrystallization). The solid obtained was identified as 6-chloro-3-methylthio-2-pyridinecarbonitrile (14.5 g). The retained filtrates were combined and concentrated to give 17.5 g of a mixture of 6-chloro-3-methylthio-2-pyridinecarbonitrile and 3-chloro-6-methylthio-2-pyridinecarbonitrile in a ratio of about 3:1, respectively. The isomers were then separated on a Waters Prep LC500 instrument using 15% ethyl acetate in hexane.

The melting point of the 6-chloro-3-methylthio-2-pyridinecarbonitrile isomer was found to be 115°–118° C., while 3-chloro-6-methylthio-2-pyridinecarbonitrile was found to have a melting point (m.p.) of 76°–80° C.

EXAMPLE 2

Preparation of
6-chloro-3-ethylthio-2-pyridinecarbonitrile;
3-chloro-6-ethylthio-2-pyridinecarbonitrile; and
3,6-bis-ethylthio-2-pyridinecarbonitrile In a reaction flask with condenser, mechanical stirrer, thermometer and dropping funnel were placed 53.4 g of 3,6-dichloro-2-pyridinecarbonitrile and 300 ml of DMSO. The mixture was chilled to about 10°–15° C. and then 19.8 g of ethanethiol was added. While maintaining the temperature at <20° C., 34.8 g of t-BuOK in 300 ml of THF was added in small portions. After the addition was complete, the reaction mixture was warmed to 20° C. and stirred for about 40 hrs. The reaction mixture was then poured onto about 2 kilograms (kg) of ice, stirred and filtered leaving a solid residue. The residue was washed with water, dissolved in $CH_2Cl_2$, dried over $MgSO_4$, concentrated and diluted with hexane to give 19.0 g of 6-chloro-3-ethylthio-2-pyridinecarbonitrile. The filtrate was concentrated and separated on a Water's Prep LC 500 instrument using 15% ethyl acetate in hexane to give another 10.1 g of the same isomer. Total yield of 6-chloro-3-ethylthio-2-pyridinecarbonitrile was 29.1 g (46.5%), m.p. 79°–81° C. Further separation on the Prep LC 500 instrument gave a small amount of 3-chloro-6-ethylthio-2-pyridinecarbonitrile (m.p. 46°–48° C.) and 3,6-bis-ethylthio-2-pyridinecarbonitrile (m.p. 63°–64° C.).

EXAMPLE 3

Preparation of
6-chloro-3-propylthio-2-pyridinecarbonitrile;
3-chloro-6-propylthio-2-pyridinecarbonitrile; and
3,6-bis-propylthio-2-pyridinecarbonitrile By following a procedure substantially the same as that described in Example 2, 3,6-dichloro-2-pyridinecarbonitrile (51.9 g) was reacted with 22.9 g of propanethiol in the presence of t-BuOK (33.6 g) in about 750 ml of THF. Utilizing appropriate separation techniques, the following compounds were obtained: 6-chloro-3-propylthio-2-pyridinecarbonitrile, boiling point (b.p.) 120° C. at 0.4 mm Hg; 3-chloro-6-propylthio-2-pyridinecarbonitrile, b.p. 120° C. at 0.3 mm Hg; 3,6-bis-propylthio-2-pyridinecarbonitrile, m.p. 49°–51° C.

EXAMPLE 4

2,5-Dichloro-4-pyridinecarboxaldehyde Oxime

A solution of lithium di-isopropylamide was prepared by the addition of 100 ml of 1.5 molar (M) butyllithium (in a hexane solution) to 14.2 g of di-isopropylamine in 100 ml of THF at less than −30° C. After stirring for 20 minutes the solution was cooled to below −70° C. and a solution of 20.8 g of 2,5-dichloropyridine in 56 ml of THF was added at such a rate that the temperature was maintained at below −70° C. After the addition was complete, the reaction temperature was stirred at below −70° C. for 30 minutes. A solution of 13.2 g of DMF in 30 ml THF was added at the same temperature and stirred for an additional 30 minutes. The reaction mixture was allowed to warm to room temperature then poured into a mixture containing 250 g of ice and 45 ml of concentrated HCl and stirred for 15 minutes. The acidic solution was neutralized to about pH 6–7 with 3 normal (N) NaOH. The organic layer was separated and the aqueous layer extracted with ethyl ether. The organic solutions were combined, washed with saturated NaCl solution, dried and evaporated to dryness to give about 22 g of 2,5-dichloro-4-pyridinecarboxaldehyde. This aldehyde was dissolved in 100 ml of 2-propanol, mixed with 13.8 g of hydroxylamine hydrochloride and 20 drops of concentrated HCl and heated on a steambath for 1 hour. The mixture was then poured onto 200 g of ice, stirred well and filtered leaving a solid residue. The solid was vacuum dried to give 22.8 g (85%) of the desired 2,5-dichloro-4-pyridinecarboxaldehyde oxime

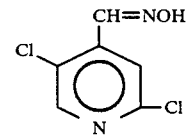

m.p. 173°–174° C.

EXAMPLE 5

2,5-Dichloro-4-pyridinecarbonitrile

To 100 ml of acetonitrile was added 24.5 g of $POCl_3$, followed by 27.1 g of 2,5-dichloro-4-pyridinecarboxaldehyde oxime (prepared as described in Example 4). The reaction mixture was heated at reflux temperature for 1 hour, then cooled and poured onto 300 g of ice.

The pH of the mixture was adjusted to about pH 6 with K$_2$CO$_3$ and filtered. The filtrate was extracted with 100 ml of CH$_2$Cl$_2$. The filter cake and the CH$_2$Cl$_2$ solution were combined, diluted with equal volumes of hexane, treated with charcoal, dried, and concentrated. The residue was purified by distillation on a Kugelrohr distillation apparatus (boiling point 80° C. at 0.2 mm pressure) to give 19.0 g (77%) of the desired 2,5-dichloro-4-pyridinecarbonitrile as a white solid, m.p. 58°–60° C.

EXAMPLE 6

Preparation of 2-chloro-5-ethylthio-4-pyridinecarbonitrile and 5-chloro-2-ethylthio-4-pyridinecarbonitrile A solution of 2.77 g of ethanethiol in 30 ml of 2-propanol was added to a mixture containing 7.7 g of 2,5-dichloro-4-pyridinecarbonitrile and 3.08 g of K$_2$CO$_3$ in 60 ml of 2-propanol at 0° C. The reaction mixture was allowed to warm to room temperature and then stirred for 4 days, after which it was poured onto 200 g of ice, stirred and extracted with CH$_2$Cl$_2$. Thin layer chromatography (using 10 percent ethyl acetate in hexane) disclosed the presence of three components. The CH$_2$Cl$_2$ solution was dried and concentrated to 25 ml and then diluted with 12.5 ml of hexane to give a crystalline material which was separated by filtration and identified as 2-chloro-5-ethylthio-4-pyridinecarbonitrile. The filtrate was concentrated and separated on a Water's Prep LC 500 instrument eluted with 2 percent ethyl acetate in hexane. Cuts of identical components were combined, evaporated and recrystallized to give 0.94 g (18%) of 5-chloro-2-ethylthio-4-pyridinecarbonitrile, (m.p. 103°–104° C.) and 3.33 g (64.5%) of 2-chloro-5-ethylthio-4-pyridinecarbonitrile (m.p. 112°–114° C.). The third component was identified as unreacted starting material.

EXAMPLE 7

5-Chloro-2-ethylthio-4-pyridinecarboxaldehyde oxime

5-Chloro-2-ethylthiopyridine (prepared by known procedures from 2,5-dichloropyridine and ethanethiol) was used in a procedure substantially the same as that described in Example 4, to prepare 5-chloro-2-ethylthio-4-pyridinecarboxaldehyde. The corresponding oxime was then prepared by reacting the 5-chloro-2-ethylthio-4-pyridinecarboxaldehyde with hydroxylamine hydrochloride in the presence of acid as described in Example 4, above. The resulting 5-chloro-2-ethylthio-4-pyridinecarboxaldehyde oxime had a melting point of 128°–130° C.

EXAMPLE 8

5-Chloro-2-ethylthio-4-pyridinecarbonitrile

Using the same procedure described in Example 5, 5-chloro-2-ethylthio-4-pyridinecarboxaldehyde oxime was dehydrated to the desired 5-chloro-2-ethylthio-4-pyridine-carbonitrile having a melting point of 103°–104° C.

Using the procedures described herein, the following additional compounds were prepared:

EXAMPLE 9

5-Chloro-2-methylthio-4-pyridinecarboxaldehyde oxime, m.p. 160°–162° C.

EXAMPLE 10

5-Chloro-2-methylthio-4-pyridinecarbonitrile, m.p. 100°–101° C.

EXAMPLE 11

6-Chloro-3-isopropylthio-2-pyridinecarbonitrile, b.p. 120° C. (0.025 mm Hg).

EXAMPLE 12

3-Chloro-6-isopropylthio-2-pyridinecarbonitrile, m.p. 60°–61° C.

EXAMPLE 13

3,6-Bis-isopropylthio-2-pyridinecarbonitrile, b.p. 128° C. (0.15 mm Hg).

EXAMPLE 14

6-Chloro-3-(n-butylthio)-2-pyridinecarbonitrile, m.p. 32°–34° C.

EXAMPLE 15

3-Chloro-6-(n-butylthio)-2-pyridinecarbonitrile, b.p. 113°–115° C. (0.1 mm Hg).

EXAMPLE 16

6-Chloro-3-(sec-butylthio)-2-pyridinecarbonitrile, b.p. 115° C. (0.07 mm Hg).

EXAMPLE 17

3-Chloro-6-(sec-butylthio)-2-pyridinecarbonitrile, b.p. 106° C. (0.3 mm Hg).

EXAMPLE 18

6-Chloro-3-(isobutylthio)-2-pyridinecarbonitrile, b.p. 110° C. (0.5 mm Hg).

EXAMPLE 19

3-Chloro-6-(isobutylthio)-2-pyridinecarbontrile, b.p. 98° C. (0.13 mm Hg).

The physical properties of the above examples are summarized in Table 1.

TABLE 1

| Compound Example Number | Pyridine Substituents | m.p. °C.* b.p. (mm Hg) | Calculated | | | Found | | |
|---|---|---|---|---|---|---|---|---|
| | | | % C | % H | % N | % C | % H | % N |
| 1 | 2-CN; 3-CH$_3$S; 6-Cl | 115–118 | IDENTIFIED BY NMR | | | | | |
| 1 | 2-CN; 3-Cl; 6-CH$_3$S | 76–80 | IDENTIFIED BY NMR | | | | | |
| 2 | 2-CN; 3-CH$_3$CH$_2$S; 6-Cl | 79–81 | 48.36 | 3.55 | 14.10 | 48.31 | 3.33 | 14.11 |
| 2 | 2-CN; 3-Cl; 6-CH$_3$CH$_2$S | 46–48 | 48.36 | 3.55 | 14.10 | 48.44 | 3.79 | 14.09 |
| 2 | 2-CN; 3,6-CH$_3$CH$_2$S | 63–64 | 53.54 | 5.33 | 12.49 | 53.62 | 5.43 | 12.48 |
| 3 | 2-CN; 3-CH$_3$CH$_2$CH$_2$S; 6-Cl | 120 (0.4) | 50.82 | 4.26 | 13.17 | 50.45 | 4.10 | 13.08 |
| 3 | 2-CN; 3-Cl; 6-CH$_3$CH$_2$CH$_2$S | 120 (0.3) | 50.82 | 4.26 | 13.17 | 51.59 | 4.31 | 13.10 |
| 3 | 2-CN; 3,6-CH$_3$CH$_2$CH$_2$S | 49–51 | 57.10 | 6.39 | 11.10 | 56.72 | 6.22 | 11.22 |
| 4 | 2-Cl; 4-CH=NOH; 5-Cl | 173–174 | 37.33 | 2.11 | 14.66 | 38.24 | 2.14 | 15.66 |

TABLE 1-continued

| Compound Example Number | Pyridine Substituents | m.p. °C.* b.p. (mm Hg) | Calculated % C | % H | % N | Found % C | % H | % N |
|---|---|---|---|---|---|---|---|---|
| 5 | 2-Cl; 4-CN; 5-Cl | 58–60 | 41.64 | 1.19 | 16.19 | 41.13 | 1.16 | 16.26 |
| 6 | 2-Cl; 4-CN; 5-CH$_3$CH$_2$S | 112–114 | 48.36 | 3.55 | 14.10 | 48.19 | 3.48 | 14.10 |
| 6 | 2-CH$_3$CH$_2$S; 4-CN; 5-Cl | 103–104 | 48.36 | 3.55 | 14.10 | 48.02 | 3.44 | 14.10 |
| 7 | 2-CH$_3$CH$_2$S; 4-CH=NOH; 5-Cl | 128–130 | 44.34 | 4.19 | 12.93 | 44.03 | 4.10 | 12.99 |
| 8 | 2-CH$_3$C$_2$S; 4-CN; 5-Cl | 103–104 | 48.36 | 3.55 | 14.10 | 48.37 | 3.53 | 14.23 |
| 9 | 2-CH$_3$S; 4-CH=NOH; 5-Cl | 160–162 | 41.49 | 3.48 | 13.82 | 41.36 | 3.51 | 13.76 |
| 10 | 2-CH$_3$S; 4-CN; 5-Cl | 100–101 | 45.53 | 2.73 | 15.17 | 45.16 | 2.68 | 15.10 |
| 11 | 2-CN; 3-CH$_3$CHS; 6-Cl (CH$_3$ branch) | 120 (0.025) | 50.82 | 4.26 | 13.17 | 50.58 | 4.14 | 13.16 |
| 12 | 2-CN; 3-Cl; 6-CH$_3$CHS (CH$_3$ branch) | 60–61 | 50.82 | 4.26 | 13.17 | 50.79 | 4.29 | 13.10 |
| 13 | 2-CN; 3,6-CH$_3$CHS (CH$_3$ branch) | 128 (0.15) | 57.10 | 6.39 | 11.10 | 56.52 | 6.02 | 11.05 |
| 14 | 2-CN; 3-CH$_3$(CH$_2$)$_2$CH$_2$S; 6-Cl | 32–34 | 52.97 | 4.89 | 12.35 | 52.97 | 4.74 | 12.42 |
| 15 | 2-CN; 3-Cl; 6-CH$_3$(CH$_2$)$_2$C$_2$S | 113–115 (0.1) | 52.97 | 4.89 | 12.35 | 53.51 | 4.82 | 12.70 |
| 16 | 2-CN; 3-CH$_3$CH$_2$CHS; 6-Cl (CH$_3$ branch) | 115 (0.07) | 52.97 | 4.89 | 12.35 | 52.79 | 4.42 | 12.73 |
| 17 | 2-CN; 3-Cl; 6-CH$_3$CH$_2$CHS (CH$_3$ branch) | 106 (0.3) | 52.97 | 4.89 | 12.35 | 53.13 | 4.79 | 12.32 |
| 18 | 2-CN; 3-(CH$_3$)$_2$CHCH$_2$S; 6-Cl | 110 (0.5) | 52.97 | 4.89 | 12.35 | 53.10 | 4.78 | 12.42 |
| 19 | 2-CN; 3-Cl; 6-(CH$_3$)$_2$CHCH$_2$S | 98 (0.13) | 52.97 | 4.89 | 12.35 | 53.11 | 4.82 | 12.32 |

*The values presented refer to either the melting point in degrees Centigrade or the boiling point in degrees Centigrade at a particular pressure indicated in millimeters of mercury.

EXAMPLE 20

6-(3,4-Dichlorophenoxy)-3-ethylthio-2-pyridinecarbonitrile

In a reaction flask were placed 110 ml of THF, 10 ml of DMSO and 5.6 g of t-BuOK. 3,4-Dichlorophenol (8.2 g) was added and the mixture was stirred until solution was achieved. To this was added 9.9 g of 6-chloro-3-ethylthio-2-pyridinecarbonitrile and the reaction mixture was heated at reflux temperature for about 5 hours. After cooling, the contents of the flask were poured onto 500 g of ice, stirred until the ice had melted and then filtered. The solid obtained by filtration was dissolved in CH$_2$Cl$_2$, treated with charcoal, dried and was concentrated. Upon dilution with hexane, 12.6 g (77.5%) of 6-(3,4-dichlorophenoxy)-3-ethylthio-2-pyridinecarbonitrile was obtained as a tan crystalline material, m.p. 64°–66° C. Subsequent analysis by differential scanning calorimetry indicated that the compound obtained was polymorphic and existed in two crystalline forms: one melting at 66°–69° C., and the other at 81°–87° C.

The higher melting form was isolated by the following procedure. The product obtained by the above-described process was dissolved in a volume of CH$_2$Cl$_2$ and heated to boiling. Hexane was added until the product began to oil out of solution. CH$_2$Cl$_2$ was added to the solution until a homogeneous solution was again obtained. This solution was allowed to stand overnight at room temperature resulting in the precipitation of large tan crystals. The crystals were collected and determined to be the desired 6-(3,4-dichlorophenoxy)-3-ethylthio-2-pyridinecarbonitrile, m.p. 80°–81° C.

EXAMPLE 21

3-(3,4-Dichlorophenoxy)-6-ethylthio-2-pyridinecarbonitrile

Following a procedure substantially the same as that described in Example 20, 8.0 g of 3-chloro-6-ethylthio-2-pyridinecarbonitrile was reacted with 8.2 g of 3,4-dichlorophenol in the presence of 5.6 g of t-BuOK in 60 ml of THF and 30 ml of DMSO. The reaction was allowed to proceed at boiling temperature for about 40 hours. The product, an oil, was purified by distillation on a Kugelrohr distillation apparatus, separated on a Water's Prep LC 500 instrument, and again distilled on a Kugelrohr apparatus to give about 7 g (54%) of the desired 3-(3,4-dichlorophenoxy)-6-ethylthio-2-pyridinecarbonitrile, having a boiling point (b.p.) of 160° C. at 0.01 mm Hg pressure.

Using substantially the same procedure as that described in Example 20, the compounds of Examples 22 through 26 were prepared.

EXAMPLE 22

2-(3,4-Dichlorophenoxy)-5-ethylthio-4-pyridinecarbonitrile

2-Chloro-5-ethylthio-4-pyridinecarbonitrile (4.0 g) was reacted with 3.6 g of 3,4-dichlorophenol in the presence of 2.6 g of t-BuOK in 40 ml of THF and 4 ml of DMSO. 5.5 g (84.6%) of the desired, 2-(3,4-dichlorophenoxy)-5-ethylthio-4-pyridinecarbonitrile was recovered, m.p. 68°–69° C.

EXAMPLE 23

5-(3,4-Dichlorophenoxy)-2-ethylthio-4-pyridinecarbonitrile

5-Chloro-2-ethylthio-4-pyridinecarbonitrile (5.4 g) was mixed with 5.4 g of 3,4-dichlorophenol in the presence of 3.7 g of t-BuOK in 30 ml of THF and 30 ml of DMSO. The mixture was heated at boiling temperature for about 70 hours to give 3.2 g (36%) of the desired 5-(3,4-dichlorophenoxy)-2-ethylthio-4-pyridinecarbonitrile, m.p. 79°–81° C.

EXAMPLE 24

5-(3,4-Dichlorophenoxy)-2-methylthio-4-pyridinecarbonitrile

5-Chloro-2-methylthio-4-pyridinecarbonitrile (12.0 g) was mixed with 3,4-dichlorophenol (12.7 g) in the presence of 8.75 g of t-BuOK in 70 ml of THF and 70 ml of DMSO. The mixture was heated at boiling temperature for about 48 hours to give 12.5 g (62%) of the desired, 5-(3,4-dichlorophenoxy)-2-methylthio-4-pyridinecarbonitrile, m.p. 96°–97° C.

EXAMPLE 25

6-(3,4-Dichlorophenoxy)-3-methylthio-2-pyridinecarbonitrile

6-Chloro-3-methylthio-2-pyridinecarbonitrile was mixed with 16.3 g of 3,4-dichlorophenol in the presence of 11.2 g of t-BuOK in 150 ml THF and 15 ml of DMSO. 13.4 g (54%) of the desired, 6-(3,4-dichlorophenoxy)-3-methylthio-2-pyridinecarbonitrile was recovered, m.p. 156°–158° C.

EXAMPLE 26

6-(4-Benzoylphenoxy)-3-ethylthio-2-pyridinecarbonitrile

6-Chloro-3-ethylthio-2-pyridinecarbonitrile (23.8 g) was mixed with 25.8 g of 4-benzoylphenol in the presence of 15.7 g of t-BuOK in 150 ml of THF and 30 ml DMSO. After reaction, the mixture was filtered leaving a solid residue from which 12.4 g of the desired 6-(4-benzoylphenoxy)-3-ethylthio-2-pyridinecarbonitrile (m.p. 88°–90° C.) was recovered. An additional 6.5 g of desired product was isolated from the filtrate by separation on a Water's Prep LC 500 instrument (using a 10% acetone in hexane eluant).

EXAMPLE 27

5-(3,4-Dichlorophenoxy)-2-ethylthio-3-pyridinecarbonitrile 5-(3,4-Dichlorophenoxy)-2-ethylthio-3-pyridinecarbonitrile was prepared through the following sequence of reactions:

(a) Preparation of 3,4-dichlorophenoxy-acetaldehyde diethyl acetal

Potassium hydroxide (66 g) and 3,4-dichlorophenol (163 g) were placed in a reaction flask equipped with a distillation head, dropping funnel, thermometer and mechanical stirrer. This mixture was gradually heated to achieve solution and then 250 g of chloroacetaldehyde diethyl acetal was added while the temperature was maintained at 90° C. After the addition was complete, the temperature was allowed to increase in order to distill off water and unreacted chloroacetaldehyde diethyl acetal. The distillate separated into layers which were recovered by conventional techniques. The lower layer was dried and subsequently returned to the reaction flask where it was heated (without distillation) at 190° C. for 2 hours. The contents of the reaction flask were cooled to room temperature and poured into an ice-water mixture and extracted with methylene chloride. The methylene chloride solution was washed with 300 ml of 2N NaOH, dried, and distilled. After removal of the starting material, 276.3 g of the desired, 3,4-dichlorophenoxyacetaldehyde diethyl acetal was obtained, b.p. 125° C. (0.04 mm Hg).

(b) Preparation of 2-(3,4-dichlorophenoxy)-3-dimethylamino-propenal

Dimethylformamide (29.2 g) was slowly added to 122.7 g of $POCl_3$ in a reaction flask. After the addition was complete, the mixture was heated to 80° C. while 3,4-dichlorophenoxyacetaldehyde diethyl acetal (55.8 g) was added, and the resulting mixture was then heated for an additional two hours at about 80°–85° C. The reaction mixture was cooled to room temperature and poured into about 400 g of potassium carbonate in an ice-water mixture and then extracted with methylene chloride. The methylene chloride extract was then dried and concentrated to a dark oil which solidified upon dilution with ethyl acetate. 22.1 g of the desired, 2-(3,4-dichlorophenoxy)-3-dimethylamino-propenal was obtained and subsequently identified by NMR spectroscopy.

(c) Preparation of 5-(3,4-dichlorophenoxy)-2-hydroxy-3-pyridinecarboxamide 2-(3,4-Dichlorophenoxy)-3-dimethylaminopropenal (13 g), malonamide (5.6 g), and t-BuOK (6.2 g) were mixed in 50 ml of DMSO and heated at 45° C. for 30 minutes. This mixture was then stirred at room temperature for an additional 24 hours after which it was poured into 200 g of an ice-water mixture and acidified with concentrated HCl. A solid formed which was collected by centrifugation, vacuum dried, and recrystallized from 2-propanol to give 6.5 g of the desired 5-(3,4-dichlorophenoxy)-2-hydroxy-3-pyridinecarboxamide, m.p. 246°–249° C.

(d) Preparation of 2-chloro-5-(3,4-dichlorophenoxy)-3-pyridinecarbonitrile

To 19.5 g of phenylphosphonic dichloride was added 6.0 g of 5-(3,4-dichlorophenoxy)-2-hydroxy-b 3-pyridinecarboxamide, followed by the addition of $PCl_5$ (4.2 g). The mixture was heated at 180° C. for 1 hour, then at 140° C. for an additional 2 hours, after which it was cooled to room temperature and poured into a mixture of water/$CH_2Cl_2$ (to which ice was added periodically). This mixture was then dried, concentrated, and distilled on a Kugelrohr distillation apparatus to give 3.7 g of the desired, 2-chloro-5-(3,4-dichlorophenoxy)-3-pyridinecarbonitrile as an oil, which solidified upon standing, m.p. 76°–78° C.

(e) Preparation of 5-(3,4-dichlorophenoxy)-2-ethylthio-3-pyridinecarbonitrile

THF (25 ml), and NaOH (0.8 g) were mixed in a reaction flask to which was added 1.24 g of ethanethiol (previously chilled in an ice-salt bath). This mixture was stirred at room temperature until all of the NaOH was dissolved. Separately, 4.5 g of 2-chloro-5-(3,4-dichlorophenoxy)-3-pyridinecarbonitrile was dissolved in 25 ml of THF and then added to the previously prepared ethanethiol mixture. This combination was then stirred at room temperature for 30 minutes and then heated to boiling for 2 hours after which it was allowed to cool and then poured into 300 g of ice. A precipitate formed which was collected by filtration and subsequently recrystallized from a $CH_2Cl_2$/hexane mixture to give 4.3 g of the desired 5-(3,4-dichlorophenoxy)-2-ethylthio-3-pyridinecarbonitrile, m.p. 80°–81° C.

EXAMPLE 28

2-(3,4-Dichlorophenoxy)-5-ethylthio-3-pyridinecarbonitrile (a) Preparation of 5-amino-2-(3,4-dichlorophenoxy)-3-pyridinecarbonitrile 2-(3,4-Dichlorophenoxy)-5-nitro-3-pyridinecarbonitrile was prepared by the reaction of 3,4-dichlorophenol with 2-chloro-5-nitro-3-pyridinecarbonitrile, a compound known to the art (see *J. Am. Chem. Soc.* 77:1045, 1955). 20.5 g of the 2-(3,4-dichlorophenoxy)-5-nitro-3-pyridinecarbonitrile was hydrogenated in a Parr apparatus using 10 g of Raney nickel catalyst (previously washed with water until the pH of the washes was 7) in 200 ml of alcohol at room temperature under pressure (45 pounds per square inch). The catalyst and solvent were subsequently removed, leaving a solid residue which was crystallized from a $CH_2Cl_2$/hexane mixture and then from a $CHCl_3$/hexane mixture to give 7.2 g of the desired, 5-amino-2-(3,4-dichlorophenoxy)-3-pyridinecarbonitrile, m.p. 135°–137° C.

(b) 2-(3,4-Dichlorophenoxy)-5-ethylthio-3-pyridinecarbonitrile

5-Amino-2-(3,4-dichlorophenoxy)-3-pyridinecarbonitrile was diazotized by dissolving 6.8 g of said compound in a mixture containing 10.6 ml of $HBF_4$ (48% aqueous solution) and 20 ml of ethanol. To this mixture was slowly added 1.83 g of $NaNO_2$ in 5 ml of water at −10° C. After the addition was complete, a heavy paste formed and was allowed to stand at −10° C. for about 10 minutes. The paste was then diluted with 50 ml of ethyl ether and filtered. The filter cake was then added in small portions to a solution consisting of ethanethiol (1.65 g) and NaOH (1.06 g) in 50 ml of acetonitrile which had been warmed to 30° C. After this addition was complete, the whole mixture was heated on a steambath for about 40 minutes, cooled, diluted with $CH_2Cl_2$, and then dried. The solvent was then removed, leaving a residue which was separated on a Water's Prep LC 500 instrument by eluting with 5% ethyl acetate in hexane. The eluate was collected and crystallized from $CH_2Cl_2$/hexane to give 0.9 g (11%) of the desired 2-(3,4-dichlorophenoxy)-5-ethylthio-3-pyridinecarbonitrile, m.p. 114°–115° C.

A second component, eluted with 10% ethylacetate in hexane was identified to be 2-(3,4-dichlorophenoxy)-3-pyridinecarbonitrile.

EXAMPLE 29

6-(3,4-Dichlorophenoxy)-3-methylsulfinyl-2-pyridinecarbonitrile 6-(3,4-Dichlorophenoxy)-3-methylthio-2-pyridinecarbonitrile (3.1 g) was mixed in 50 ml of $CHCl_3$. The temperature of this mixture was maintained at about 15°–25° C. while 12.5 g of m-chloroperbenzoic acid was added in small portions. After the addition was complete, the mixture was washed with 50 ml of 3N NaOH, dried over $K_2CO_3$ and concentrated. Dilution with a volume of hexane gave 2.7 g (82.5%) of the desired, 6-(3,4-dichlorophenoxy)-3-methylsulfinyl-2-pyridinecarbonitrile, m.p. 165°–167° C.

EXAMPLE 30

6-(3,4-Dichlorophenoxy)-3-methylsulfinyl-2-pyridinecarboxamide 6-(3,4-Dichlorophenoxy)-3-methylthio-2-pyridinecarbonitrile (4.1 g) was suspended in 30 ml of trifluoroacetic acid (TFA) and cooled to about 5°–10° C. Hydrogen peroxide (30% solution) was added in a dropwise manner with stirring. After the addition was complete, stirring was continued for an additional hour. The reaction mixture was then diluted with ice and filtered, leaving a solid residue. The residue was dissolved in $CH_2Cl_2$, dried and concentrated. Upon dilution with a mixture of ethyl acetate and hexane, 2.7 g (59%) of the desired, 6-(3,4-dichlorophenoxy)-3-methylsulfinyl-2-pyridinecarboxamide was obtained, m.p. 185°–187° C.

EXAMPLE 31

6-(3,4-Dichlorophenoxy)-3-ethylsulfinyl-2-pyridinecarbonitrile

Using the procedure described by Oae et al. in *Bull. Chem. Soc. Japan*, 39, 364 (1966), 7.5 g of 6-(3,4-dichlorophenoxy)-3-ethylthio-2-pyridinecarbonitrile was oxidized with 12.1 g of DABCO® dibromide. Recrystallization from methylene chloride/ethyl acetate gave 3.8 g (48%) of the desired 6-(3,4-dichlorophenoxy)-3-ethylsulfinyl-2-pyridinecarbonitrile, m.p. 138°–144° C.

EXAMPLE 32

6-(3,4-Dichlorophenoxy)-3-methylsulfonyl-2-pyridinecarbonitrile 6-(3,4-Dichlorophenoxy)-3-methylthio-2-pyridinecarbonitrile (3.1 g) was suspended in 50 ml of $CHCl_3$ and cooled in an ice-water bath. 5.4 g of m-chloroperbenzoic acid was added in small portions and then stirred for about five hours. The mixture was diluted with 30 ml $CH_2Cl_2$ and extracted with 50 ml of 3N NaOH, washed with water, and then dried over $Na_2CO_3$. The resulting solution was concentrated and then diluted with a volume of hexane to give 2.9 g (85%) of the desired, 6-(3,4-dichlorophenoxy)-3-methylsulfonyl-2-pyridinecarbonitrile, m.p. 168°–170° C.

EXAMPLE 33

6-(3,4-Dichlorophenoxy)-3-ethylsulfonyl-2-pyridinecarbonitrile 6-(3,4-Dichlorophenoxy)-3-ethylthio-2-pyridinecarbonitrile (7.9 g) was suspended in 15 ml of acetic acid and cooled. To this was added 100 ml of a sodium hypochlorite solution (containing 70 millimoles NaOCl) in small portions such that the temperature of the mixture did not rise above 40° C. After the addition was complete, the mixture was stirred at room temperature for 1 hour and then filtered leaving a solid residue. The residue was dissolved in $CH_2Cl_2$, dried, and then concentrated. Subsequent dilution with hexane gave a solid which was recrystallized from a mixture of CH2Cl2/hexane leaving 2.6 g (30%) of the desired 6-(3,4-dichlorophenoxy)-3-ethylsulfonyl-2-pyridinecarbonitrile, m.p. 150°–151° C.

By utilizing procedures described herein, the following compounds were also prepared.

EXAMPLE 34

6-(3,4-Dichlorophenoxy)-3-propylthio-2-pyridinecarbonitrile

6-Chloro-3-propylthio-2-pyridinecarbonitrile (12.8 g) was mixed with 10.6 g of 3,4-dichlorophenol in the presence of 7.3 g of t-BuOK in DMSO (10 ml) and THF (100 ml). The desired, 6-(3,4-dichlorophenoxy)-3-propylthio-2-pyridinecarbonitrile was recovered, m.p. 67°–69° C.

EXAMPLE 35

3-(3,4-Dichlorophenoxy)-6-propylthio-2-pyridinecarbonitrile

3-Chloro-6-propylthio-2-pyridinecarbonitrile (6.2 g) was mixed with 5.7 g of 3,4-dichlorophenol and 3.9 g of t-BuOK in 30 ml of DMSO and 30 ml THF. The desired, 3-(3,4-dichlorophenoxy)-6-propylthio-2-pyridinecarbonitrile was recovered, b.p. 203° C. (at 0.2 mm Hg).

EXAMPLE 36

6-(3,4-Dichlorophenoxy)-3-isopropylthio-2-pyridinecarbonitrile, m.p. 76°–78° C.

EXAMPLE 37

3-(3,4-Dichlorophenoxy)-6-isopropylthio-2-pyridinecarbonitrile, m.p. 67°–69° C.

EXAMPLE 38

6-(3,4-Dichlorophenoxy)-3-(n-butylthio)-2-pyridinecarbonitrile, m.p. 49°–50° C.

EXAMPLE 39

3-(3,4-Dichlorophenoxy)-6-(n-butylthio)-2-pyridinecarbonitrile, b.p. 194° C. (0.1 mm Hg).

EXAMPLE 40

6-(3,4-Dichlorophenoxy)-3-(sec-butylthio)-2-pyridinecarbonitrile, m.p. 56°–58° C.

EXAMPLE 41

3-(3,4-Dichlorophenoxy)-6-(sec-butylthio)-2-pyridinecarbonitrile, m.p. 80°–81° C.

EXAMPLE 42

6-(3,4-Dichlorophenoxy)-3-(isobutylthio)-2-pyridinecarbonitrile, m.p. 77°–78° C.

EXAMPLE 43

3-(3,4-Dichlorophenoxy)-6-(isobutylthio)-2-pyridinecarbonitrile, b.p. 170° C. (0.075 mm Hg).

The physical properties of the compounds of Examples 20 through 43 are provided in Table 2 where the substituents $R(O)_mS-$, $Y^1$ and $Y^2$ are determined by reference to formula I.

TABLE 2

| Compound Example Number | * | R(O)$_m$S— R | m | * | Y$^1$ | o | Y$^2$ | m.p. °C.** b.p. (mm Hg) | Calculated % C | % H | % N | Found % C | % H | % N |
|---|---|---|---|---|---|---|---|---|---|---|---|---|---|---|
| 20$^a$ | 3 | CH$_3$CH$_2$ | 0 | 2 | CN | 6 | 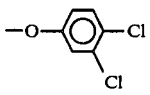 | 64–66 | 51.70 | 3.10 | 8.61 | 51.62 | 3.22 | 8.64 |
| 21 | 6 | CH$_3$CH$_2$ | 0 | 2 | CN | 3 | 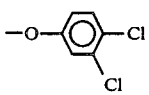 | 160(0.01) | 51.70 | 3.10 | 8.61 | 51.69 | 3.22 | 8.52 |
| 22 | 5 | CH$_3$CH$_2$ | 0 | 4 | CN | 2 | 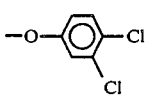 | 68–69 | 51.70 | 3.10 | 8.61 | 51.46 | 3.09 | 8.76 |
| 23 | 2 | CH$_3$CH$_2$ | 0 | 4 | CN | 5 | 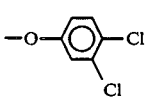 | 79–81 | 51.70 | 3.10 | 8.61 | 51.71 | 3.12 | 8.71 |
| 24 | 2 | CH$_3$ | 0 | 4 | CN | 5 | 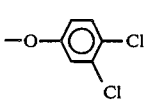 | 96–97 | 50.17 | 2.59 | 9.00 | 50.11 | 2.57 | 9.02 |
| 25 | 3 | CH$_3$ | 0 | 2 | CN | 6 | 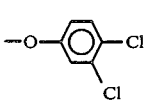 | 156–158 | 50.17 | 2.59 | 9.00 | 49.70 | 2.68 | 9.00 |
| 26 | 3 | CH$_3$CH$_2$ | 0 | 2 | CN | 6 | 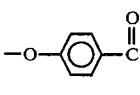 | 88–90 | 69.98 | 4.48 | 7.77 | 69.90 | 4.74 | 7.78 |

TABLE 2-continued

| Compound Example Number | R(O)ₘS— | | Y¹ | | Y² | | m.p. °C.** b.p. (mm Hg) | Calculated | | | Found | | |
|---|---|---|---|---|---|---|---|---|---|---|---|---|---|
| | * R | m | * | * | | | | % C | % H | % N | % C | % H | % N |
| 27 | 2 CH₃CH₂ | 0 | 3 CN | 5 | —O—C₆H₃Cl₂ (3,4-diCl) | | 80–81 | 51.70 | 3.10 | 8.61 | 51.32 | 3.06 | 8.60 |
| 28 | 5 CH₃CH₂ | 0 | 3 CN | 2 | —O—C₆H₃Cl₂ | | 114–115 | 51.70 | 3.10 | 8.61 | 51.35 | 3.10 | 8.99 |
| 29 | 3 CH₃ | 1 | 2 CN | 6 | —O—C₆H₃Cl₂ | | 165–167 | 47.72 | 2.46 | 8.56 | 47.39 | 2.43 | 8.57 |
| 30 | 3 CH₃ | 1 | 2 C(O)NH₂ | 6 | —O—C₆H₃Cl₂ | | 185–187 | 45.23 | 2.92 | 8.11 | 45.07 | 2.97 | 8.28 |
| 31 | 3 CH₃CH₂ | 1 | 2 CN | 6 | —O—C₆H₃Cl₂ | | 138–144 | 49.28 | 2.95 | 8.21 | 49.48 | 2.99 | 8.21 |
| 32 | 3 CH₃ | 2 | 2 CN | 6 | —O—C₆H₃Cl₂ | | 168–170 | 45.50 | 2.35 | 8.16 | 45.35 | 2.37 | 8.31 |
| 33 | 3 CH₃CH₂ | 2 | 2 CN | 6 | —O—C₆H₃Cl₂ | | 150–151 | 47.07 | 2.82 | 7.84 | 46.76 | 2.70 | 7.74 |
| 34 | 3 CH₃CH₂CH₂ | 0 | 2 CN | 6 | —O—C₆H₃Cl₂ | | 67–69 | 53.11 | 3.56 | 8.26 | 52.66 | 3.45 | 8.28 |
| 35 | 6 CH₃CH₂CH₂ | 0 | 2 CN | 3 | —O—C₆H₃Cl₂ | | 203(0.2) | 53.11 | 3.56 | 8.26 | 53.59 | 3.68 | 8.21 |
| 36 | 3 (CH₃)₂CH | 0 | 2 CN | 6 | —O—C₆H₃Cl₂ | | 76–78 | 53.11 | 3.56 | 8.26 | 53.07 | 3.56 | 8.23 |
| 37 | 6 (CH₃)₂CH | 0 | 2 CN | 3 | —O—C₆H₃Cl₂ | | 67–69 | 53.11 | 3.56 | 8.26 | 53.34 | 3.53 | 8.07 |
| 38 | 3 CH₃(CH₂)₃ | 0 | 2 CN | 6 | —O—C₆H₃Cl₂ | | 49–50 | 54.41 | 3.91 | 7.93 | 54.39 | 4.01 | 8.11 |
| 39 | 6 CH₃(CH₂)₃ | 0 | 2 CN | 3 | —O—C₆H₃Cl₂ | | 194(0.1) | 54.41 | 3.91 | 7.93 | 53.85 | 3.98 | 7.83 |

TABLE 2-continued

| Compound Example Number | R(O)$_m$S— R [*] | m | Y$^1$ [*] | Y$^2$ [*] | m.p. °C.[**] b.p. (mm Hg) | Calculated %C | %H | %N | Found %C | %H | %N |
|---|---|---|---|---|---|---|---|---|---|---|---|
| 40 | 3  CH$_3$–CH$_3$CH$_2$CH | 0 | 2 CN | 6  —O—C$_6$H$_3$Cl$_2$ (Cl, Cl) | 56–58 | 54.41 | 3.91 | 7.93 | 54.40 | 3.79 | 7.98 |
| 41 | 6  CH$_3$–CH$_3$CH$_2$CH | 0 | 2 CN | 3  —O—C$_6$H$_3$Cl$_2$ (Cl, Cl) | 80–81 | 54.41 | 3.91 | 7.93 | 54.87 | 3.91 | 7.99 |
| 42 | 3  CH$_3$–CH$_3$CHCH$_2$ | 0 | 2 CN | 6  —O—C$_6$H$_3$Cl$_2$ (Cl, Cl) | 77–78 | 54.41 | 3.91 | 7.93 | 54.57 | 3.96 | 8.00 |
| 43 | 6  CH$_3$–CH$_3$CHCH$_2$ | 0 | 2 CN | 3  —O—C$_6$H$_3$Cl$_2$ (Cl, Cl) | 170(0.075) | 54.41 | 3.91 | 7.93 | 54.99 | 4.06 | 7.92 |

[*]Number represents the ring position of the substituent relative to formula I.
[**]The values presented refer to either the melting point in degrees Centigrade or the boiling point in degrees Centigrade at a particular pressure indicated in millimeters of mercury.
[a]Polymorphic form.

The antiviral compounds of this invention have been found to be particularly effective against picornaviruses, i.e., the small ribonucleic acid viruses. The picornaviruses include viruses such as Coxsackieviruses, polio viruses, various Rhinoviruses and a number of plant disease viruses. There is some compound-to-compound variation in antiviral potency and spectrum of antiviral activity, and in toxicity and side effects, as illustrated below.

Antiviral activity for the subject compounds was demonstrated utilizing the following tissue culture testing procedure:

Monolayered HeLa cells in 16 millimeter (mm) tissue culture dishes were treated with 1 ml of culture medium (Eagles medium supplemented with fetal calf serum) containing subject compound at an appropriate concentration or containing no compound at all. Culture media such as those described herein are more fully described in standard texts, as for example, Kuchler's *Biochemical Methods in Cell Culture and Virology*, Dowden, Hutchinson and Ross, Inc., Stroudsberg, PA (1977). Following treatment, the cells were challenged with 0.05 ml of rhinovirus type 1A (RV-1A), rhinovirus type 2 (RV-2) or Coxsackie A$_{21}$ virus (Cox A$_{21}$) in culture medium. Some of the compounds were also tested against rhinovirus type 39 (RV-39), rhinovirus type 64 (RV-64) or polio virus type 2 (Polio-2). Cell controls received no viruses. Cultures were observed for compound cytotoxicity and viral cytopathic effect (CPE) at 48 and 72 hours post-treatment.

In addition, some of the compounds were tested in animals utilizing the following procedure, hereinafter referred to as the "Single Oral Dose" test. Swiss male mice, 8–12 grams in weight were challenged intraperitoneally (IP) with 0.2 ml of a normally lethal dose (i.e., a virus dose sufficient to cause ≅80–100% mortality in infected animals within 10 days of challenge) of Cox A$_{21}$, in phosphate buffered saline containing 1% heat inactivated fetal calf serum. Three hours later the mice were treated orally (p.o.) with 0.2 ml of compound suspended in 0.5% methylcellulose (Methocel ®) or with 0.2 ml of 0.5% Methocel ® containing no compound. Compound solutions administered had a concentration of 5 milligrams/milliliter (mg/ml), 15 mg/ml, 20 mg/ml or 30 mg/ml. Thus 0.2 ml of compound suspended in 0.5 percent Methocel ® represents a dosage of 100 milligrams/kilogram (mg/kg), 300 mg/kg, 400 mg/kg or 600 mg/kg, respectively. Mice were observed daily for 7–10 days post-challenge and deaths recorded. A modified Mantel-Haenzel combined chi-square ($X^2$) procedure was used to determine significant difference between virus control and treated groups. Chi-square values greater than 3.84 are considered significant (95% confidence level) in this test.

Some of the compounds were also tested in animals utilizing the following procedure, hereinafter referred to as the "Continuous Oral Feeding" test. Coxsackie A$_{21}$ virus grown on HeLa cells was administered at a concentration that produces 80 to 100% deaths in mice weighing 8 to 12 grams within 10 days, when the mice are injected (IP) with 0.2 ml of virus preparation. Mice were placed on diets containing test compound dispersed in plain commercially available rodent mash chow at a concentration of 0.06% (weight percent) on day 0. On day 1 the mice were challenged with the virus preparation, 0.2 ml/mouse, (IP). Deaths in both control and experimental groups were recorded for the 10 days and the results analyzed by a chi-square ($X^2$) test. Chi-square values greater than 3.84 indicate the compound is active (95% confidence level).

The results obtained from the testing described above are summarized in Table 3.

TABLE 3

| Example Number | Cytotoxicity[a] ($\mu$g/ml) | Tissue Culture Testing[b] ($\mu$g/ml) | | | | | | Single Oral Dose | | Continuous Oral Feeding | |
|---|---|---|---|---|---|---|---|---|---|---|---|
| | | RV-1A | RV-2 | CoxA$_{21}$ | RV-39 | Polio-2 | RV-64 | Dose (mg/kg) | $X^2$ | Dose[c] | $X^2$ |
| 20[d] | >12.5 | 3.13 | 3.13 | 0.03 | 6.25 | <0.78 | 12.5 | 600 | 12.7 | 0.06% | 6.5 |
| 21 | 2.5 | 2.5 | 0.6 | 0.6 | | | 2.5 | 600 | 16.4 | | |
| 22 | 50 | >50 | 2.5 | 0.63 | | | NA | 600 | 12.684 | | |
| 23 | 50 | >50 | 2.5 | 2.5 | | | NA | 300 | 8.811 | | |
| 24 | >50 | >50 | >50 | 1.25 | | | >50 | 600 | 4.214 | | |
| 25 | >50 | 25 | NA | <3.1 | | | | 600 | 3.0 | | |
| 26 | 50 | 25 | <3.1 | <3.1 | | | NA | 600 | 5.7 | 0.06% | 27.5 |
| 27 | >50 | NA | NA | <3.13 | | | NA | 400 | 0.922 | | |
| 28 | >50 | >50 | >50 | 1.25 | | | >50 | 600 | 2.986 | | |
| 29 | >50 | 12.5 | 12.5 | 12.5 | | | | | | | |
| 30 | 25 | 6.3 | 6.3 | <3.1 | | | | 100 | 6.6 | | |
| 31 | 50 | 12.5 | 12.5 | <3.1 | | | | 600 | 26.6 | | |
| 32 | >12.5 | 6.25 | 6.25 | >50 | >12.5 | >12.5 | 3.13 | 600 | 8.5 | 0.06% | 10.1 |
| 33 | 50 | NA | <3.1 | <3.1 | | | NA | 600 | 0.0 | | |
| 34 | >50 | 1.56 | 3.13 | 0.08 | 25 | 1.56 | >12.5 | 600 | 17.0 | | |
| 35 | 50 | 0.78 | 12.5 | <3.13 | 12.5 | 12.5 | >12.5 | 600 | 1.3 | | |
| 36 | 12.5 | ≦1.56 | ≦1.56 | <1.56 | 1.56 | | 3.13 | 600 | 10.806 | | |
| 37 | ≧25 | 3.13 | <1.56 | <1.56 | | | ≦1.56 | 600 | 3.111 | | |
| 38 | >25 | 12.5 | 6.25 | <1.56 | | | 12.5 | 600 | 2.532 | | |
| 39 | ≧25 | >25 | 3.13 | 1.56 | | | 12.5 | 600 | 5.999 | | |
| 40 | >25 | 1.56 | 1.25 | 0.16 | 10 | | 1.56 | 600 | 4.598 | | |
| 41 | >25 | 6.25 | <1.56 | ≦1.56 | | | <1.56 | 600 | 0.394 | | |
| 42 | >25 | 12.5 | 6.25 | <1.56 | | | 6.25 | 600 | 1.371 | | |
| 43 | ≧25 | 12.5 | ≦1.56 | 1.56 | | | 3.13 | 600 | 2.019 | | |

[a]Cytotoxicity figures represent the concentration of the compound, micrograms/milliliter ($\mu$g/ml), found to be toxic to the cell.
[b]Lowest concentration of the compound ($\mu$g/ml) necessary to cause a 50 percent reduction in cytopathic effect.
[c]Percent (by weight) of test compound in the diet fed to test animals.
[d]Polymorphic form.
The symbol "NA" indicates that the compound was not active against that particular virus at the standard test conditions; "<" means "less than"; ">" means "greater than"; "≦" means "less than or equal to"; "≧" means "greater than or equal to".

The data set forth in Table 3 illustrates the antiviral activity of representative compounds falling within the scope of the present invention.

The tissue culture test data indicate that all of the compounds tested are active against at least one of the three test viruses (RV-1A, RV-2, or Cox A$_{21}$). In addition, several of the compounds tested exhibited antiviral activity with respect to test viruses RV-39, RV-64 or Polio-2.

Further, some of the compounds have demonstrated (at the 95% confidence level, i.e., having a $X^2$ value greater than 3.84) that they are active antiviral compounds in testing with mice as evidenced by the "Single Oral Dose" and "Continuous Oral Feeding" tests.

In using the subject compounds, a virus and/or virus host cell is contacted with an amount of one or more of the compounds effective to inhibit the virus. In antiviral applications carried out in non-living environments, contacting should be carried out in a manner which ensures continued presence of an effective amount of the compound when subsequent contact with host cells occurs. Preferably the compounds are used by contacting the host cells with an effective antiviral amount (i.e., the amount which must be employed to achieve significant viral inhibition) of one or more of the compounds. The contacting can be carried out directly, as by addition of the compound to cells in tissue culture, to inhibit contaminating picornaviruses. Contacting can also be carried out by administering an antiviral dosage of a compound of the invention to an animal (preferably, a mammal). The compounds can be administered to animals parenterally (for example, by intraperitoneal, subcutaneous or intravenous injection), topically (for example, used in an aerosol or skin lotion, or administered intranasally or buccally), rectally or orally, and the oral antiviral activity of certain of the compounds is a feature of the invention. In such applications, an effective antiviral dose of one or more of the compounds is administered to an animal. Selection of the compound or compounds for administration to animals in particular cases is dictated by considerations such as toxicity, mutagenicity, ease of administration, antiviral activity (potency), stability, compatibility with suitable carriers, etc.

The exact amount of the compound or compounds to be employed, i.e., the amount of the subject compound or compounds sufficient to provide the desired effect, depends on various factors such as the compound employed; the method of contacting or administration; the size, age and species of animal; the route, time and frequency of administration; the virus or viruses involved, and whether or not the compound is administered prophylactically or is administered to an infected animal to inhibit the infecting virus. In particular cases, the amount to be administered can be ascertained by conventional range finding techniques, for example, by observing the effect produced at different rates using conventional virus assay procedures.

The compounds are preferably administered in the form of a composition comprising the compound in admixture with a pharmaceutically-acceptable carrier, i.e., a carrier which is chemically inert to the active compound and which has no detrimental side effects or toxicity under the conditions of use. As shown above, the compounds, when administered to tissue culture medium, exhibit significant antiviral activity at low concentrations, as for example, the finding that a concentration of 6.25 $\mu$g/ml or less of a subject compound was often sufficient to cause a 50 percent reduction in cytopathic effect against a particular test virus in the tissue culture testing.

Such compositions can contain from about 0.00001 percent by weight or less to about 99 percent by weight of one or more of the active compound(s) in combination with a pharmaceutically-acceptable carrier.

Preferred compositions include compositions containing from about 0.00001 to about 0.0025 to about 0.05 to about 0.25 to about 0.5 to about one to about 10 to about 25 to about 50 percent by weight of one or more of the active compound(s) in a pharmaceutically-acceptable carrier.

The compositions can be in solid forms such as tablets, capsules, granulations, feed mixes, feed supplements and concentrates, powders, granules, or the like; as well as liquid forms such as sterile injectable suspensions, orally administered suspensions, or solutions. The pharmaceutically-acceptable carriers can include excipients such as surface active dispersing agents, suspending agents, tableting binders, lubricants, flavors and colorants. Suitable excipients are disclosed, for example, in tests such as Remington's Pharmaceutical Sciences, Fourteenth Edition, Mack Publishing Co., Easton, PA (1970).

What is claimed is:

1. A compound of the formula:

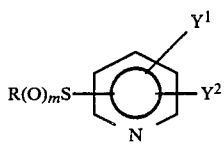

wherein $Y^1$ is cyano; $Y^2$ is substituted phenoxy or unsubstituted phenoxy wherein said substituted phenoxy moiety is a phenoxy group mono-substituted with a benzoyl radical or substituted with from 1 to 3 substituents selected from the group consisting of fluoro, chloro, bromo, or iodo; and, relative to the $R(O)_mS$— substituent, R is lower alkyl of from 1 to 6 carbon atoms, both inclusive, and m is the integer 0, 1, or 2; and the $Y^2$ substituent and the $R(O)_mS$— substituent are in para orientation with respect to one another.

2. The compound of claim 1 wherein $Y^1$ is cyano, $Y^2$ is a dichloro-substituted phenoxy moiety, and relative to the $R(O)_mS$— substituent R is lower alkyl of from one to four carbon atoms both inclusive and m is the integer 0, 1 or 2.

3. The compound of claim 2 wherein $Y^1$ is cyano, $Y^2$ is a dichloro-substituted phenoxy moiety, and relative to the $R(O)_mS$— substituent R is lower alkyl of from two to four carbon atoms both inclusive, and m is the integer 0.

4. The compound of claim 1 which is 6-(4-benzoylphenoxy)-3-ethylthio-2-pyridinecarbonitrile.

5. The compound of claim 2 which is 5-(3,4-dichlorophenoxy)-2-methylthio-4-pyridinecarbonitrile.

6. The compound of claim 2 which is 6-(3,4-dichlorophenoxy)-3-methylthio-2-pyridinecarbonitrile.

7. The compound of claim 2 which is 6-(3,4-dichlorophenoxy)-3-methylsulfinyl-2-pyridinecarbonitrile.

8. The compound of claim 2 which is 6-(3,4-dichlorophenoxy)-3-ethylsulfinyl-2-pyridinecarbonitrile.

9. The compound of claim 2 which is 6-(3,4-dichlorophenoxy)-3-methylsulfonyl-2-pyridinecarbonitrile.

10. The compound of claim 2 which is 6-(3,4-dichlorophenoxy)-3-ethylsulfonyl-2-pyridinecarbonitrile.

11. The compound of claim 3 which is 6-(3,4-dichlorophenoxy)-3-propylthio-2-pyridinecarbonitrile.

12. The compound of claim 3 which is 3-(3,4-dichlorophenoxy)-6-propylthio-2-pyridinecarbonitrile.

13. The compound of claim 3 which is 6-(3,4-dichlorophenoxy)-3-ethylthio-2-pyridinecarbonitrile.

14. The compound of claim 3 which is 3-(3,4-dichlorophenoxy)-6-ethylthio-2-pyridinecarbonitrile.

15. The compound of claim 3 which is 2-(3,4-dichlorophenoxy)-5-ethylthio-4-pyridinecarbonitrile.

16. The compound of claim 3 which is 5-(3,4-dichlorophenoxy)-2-ethylthio-4-pyridinecarbonitrile.

17. The compound of claim 3 which is 5-(3,4-dichlorophenoxy)-2-ethylthio-3-pyridinecarbonitrile.

18. The compound of claim 3 which is 2-(3,4-dichlorophenoxy)-5-ethylthio-3-pyridinecarbonitrile.

19. The compound of claim 3 which is 6-(3,4-dichlorophenoxy)-3-isopropylthio-2-pyridinecarbonitrile.

20. The compound of claim 3 which is 3-(3,4-dichlorophenoxy)-6-isopropylthio-2-pyridinecarbonitrile.

21. The compound of claim 3 which is 6-(3,4-dichlorophenoxy)-3-(n-butylthio)-2-pyridinecarbonitrile.

22. The compound of claim 3 which is 3-(3,4-dichlorophenoxy)-6-(n-butylthio)-2-pyridinecarbonitrile.

23. The compound of claim 3 which is 6-(3,4-dichlorophenoxy)-3-(sec-butylthio)-2-pyridinecarbonitrile.

24. The compound of claim 3 which is 3-(3,4-dichlorophenoxy)-6-(sec-butylthio)-2-pyridinecarbonitrile.

25. The compound of claim 3 which is 6-(3,4-dichlorophenoxy)-3-(isobutylthio)-2-pyridinecarbonitrile.

26. The compound of claim 3 which is 3-(3,4-dichlorophenoxy)-6-(isobutylthio)-2-pyridinecarbonitrile.

27. A method for inhibiting picornaviruses which comprises contacting picornaviruses or picornavirus host cells with an effective picornavirus inhibiting amount of a compound of the formula:

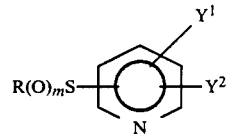

wherein $Y^1$ is cyano; $Y^2$ is substituted phenoxy or unsubstituted phenoxy wherein said substituted phenoxy moiety is a phenoxy group mono-substituted with a benzoyl radical or substituted with from 1 to 3 substituents selected from the group consisting of fluoro, chloro, bromo, or iodo; and, relative to the $R(O)_mS$— substituent, R is lower alkyl of from 1 to 6 carbon atoms, both inclusive, and m is the integer 0, 1, or 2; and the $Y^2$ substituent and the $R(O)_mS$— substituent are in para orientation with respect to one another.

28. The method of claim 27 wherein the compound is contacted with a picornavirus host cell.

29. The method of claim 27 wherein the compound is contacted with picornavirus and mammalian cells.

30. The method of claim 27 wherein $Y^1$ is cyano, $Y^2$ is a dichloro-substituted phenoxy moiety and, relative to the $R(O)_mS$— substituent, R is lower alkyl of from two to four carbon atoms both inclusive, and m is the integer zero.

31. The method of claim 30 wherein the compound is 6-(3,4-dichlorophenoxy)-3-ethylthio-2-pyridinecarbonitrile.

32. The method of claim 30 wherein the compound is 3-(3,4-dichlorophenoxy)-6-ethylthio-2-pyridinecarbonitrile.

33. The method of claim 30 wherein the compound is 2-(3,4-dichlorophenoxy)-5-ethylthio-4-pyridinecarbonitrile.

34. The method of claim 30 wherein the compound is 5-(3,4-dichlorophenoxy)-2-ethylthio-4-pyridinecarbonitrile.

35. The method of claim 30 wherein the compound is 5-(3,4-dichlorophenoxy)-2-ethylthio-3-pyridinecarbonitrile.

36. The method of claim 30 wherein the compound is 2-(3,4-dichlorophenoxy)-5-ethylthio-3-pyridinecarbonitrile.

37. The method of claim 30 wherein the compound is 6-(3,4-dichlorophenoxy)-3-isopropylthio-2-pyridinecarbonitrile.

38. The method of claim 30 wherein the compound is 3-(3,4-dichlorophenoxy)-6-isopropylthio-2-pyridinecarbonitrile.

39. The method of claim 30 wherein the compound is 6-(3,4-dichlorophenoxy)-3-(sec-butylthio)-2-pyridinecarbonitrile.

40. The method of claim 30 wherein the compound is 3-(3,4-dichlorophenoxy)-6-(sec-butylthio)-2-pyridinecarbonitrile.

41. The method of claim 30 wherein the compound is 6-(3,4-dichlorophenoxy)-3-propylthio-2-pyridinecarbonitrile.

42. A method useful for inhibiting picornaviruses which comprises administering to an animal an effective picornavirus inhibiting amount of a compound of the formula:

$$R(O)_mS-\underset{N}{\underset{|}{\bigcirc}}-Y^2 \quad {}^{Y^1}$$

wherein $Y^1$ is cyano; $Y^2$ is substituted phenoxy or unsubstituted phenoxy wherein said substituted phenoxy moiety is a phenoxy group mono-substituted with a benzoyl radical or substituted with from 1 to 3 substituents selected from the group consisting of fluoro, chloro, bromo, or iodo; and, relative to the $R(O)_mS$— substituent, R is lower alkyl of from 1 to 6 carbon atoms, both inclusive, and m is the integer, 0, 1, or 2; and the $Y^2$ substituent and the $R(O)_mS$— substituent are in para orientation with respect to one another.

43. The method of claim 42 wherein the animal is a mammal.

44. The method of claim 42 wherein the picornavirus is a Rhinovirus.

45. The method of claim 42 wherein the picornavirus is a Coxsackievirus.

46. The method of claim 44 wherein $Y^1$ is cyano, $Y^2$ is a dichloro-substituted phenoxy moiety and relative to the $R(O)_mS$— substituent, R is lower alkyl of from two to four carbon atoms both inclusive, and m is the integer zero.

47. The method of claim 46 wherein the compound is 6-(3,4-dichlorophenoxy)-3-ethylthio-2-pyridinecarbonitrile.

48. The method of claim 46 wherein the compound is 3-(3,4-dichlorophenoxy)-6-ethylthio-2-pyridinecarbonitrile.

49. The method of claim 46 wherein the compound is 2-(3,4-dichlorophenoxy)-5-ethylthio-4-pyridinecarbonitrile.

50. The method of claim 46 wherein the compound is 5-(3,4-dichlorophenoxy)-2-ethylthio-4-pyridinecarbonitrile.

51. The method of claim 46 wherein the compound is 5-(3,4-dichlorophenoxy)-2-ethylthio-3-pyridinecarbonitrile.

52. The method of claim 46 wherein the compound is 2-(3,4-dichlorophenoxy)-5-ethylthio-3-pyridinecarbonitrile.

53. The method of claim 46 wherein the compound is 6-(3,4-dichlorophenoxy)-3-isopropylthio-2-pyridinecarbonitrile.

54. The method of claim 46 wherein the compound is 3-(3,4-dichlorophenoxy)-6-isopropylthio-2-pyridinecarbonitrile.

55. The method of claim 46 wherein the compound is 6-(3,4-dichlorophenoxy)-3-(sec-butylthio)-2-pyridinecarbonitrile.

56. The method of claim 46 wherein the compound is 3-(3,4-dichlorophenoxy-6-(sec-butylthio)-2-pyridinecarbonitrile.

57. The method of claim 46 wherein the compound is 6-(3,4-dichlorophenoxy)-3-propylthio-2-pyridinecarbonitrile.

58. A composition for inhibiting picornaviruses comprising an inert carrier in combination with an effective picornavirus inhibiting amount of a compound of the formula:

$$R(O)_mS-\underset{N}{\underset{|}{\bigcirc}}-Y^2 \quad {}^{Y^1}$$

wherein $Y^1$ is cyano; $Y^2$ is substituted phenoxy or unsubstituted phenoxy wherein said substituted phenoxy moiety is a phenoxy group mono-substituted with a benzoyl radical or substituted with from 1 to 3 substituents selected from the group consisting of fluoro, chloro, bromo, or iodo; and, relative to the $R(O)_mS$— substituent, R is lower alkyl of from 1 to 6 carbon atoms, both inclusive, and m is the integer 0, 1, or 2; and the $Y^2$ substituent and the $R(O)_mS$— substituent are in para orientation with respect to one another.

59. The composition of claim 58 wherein the inert carrier is a non-toxic carrier.

60. The composition of claim 59 wherein the non-toxic carrier is a pharmaceutically-acceptable carrier.

61. The composition of claim 58 wherein $Y^1$ is cyano, $Y^2$ is a dichloro-substituted phenoxy moiety and relative to the $R(O)_mS$— substituent, R is lower alkyl of from two to four carbon atoms both inclusive, and m is the integer zero.

62. The composition of claim 61 wherein the compound is 6-(3,4-dichlorophenoxy)-3-ethylthio-2-pyridinecarbonitrile.

63. The composition of claim 61 wherein the compound is 3-(3,4-dichlorophenoxy)-6-ethylthio-2-pyridinecarbonitrile.

64. The composition of claim 61 wherein the compound is 2-(3,4-dichlorophenoxy)-5-ethylthio-4-pyridinecarbonitrile.

65. The composition of claim 61 wherein the compound is 5-(3,4-dichlorophenoxy)-2-ethylthio-4-pyridinecarbonitrile.

66. The composition of claim 61 wherein the compound is 5-(3,4-dichlorophenoxy)-2-ethylthio-3-pyridinecarbonitrile.

67. The composition of claim 61 wherein the compound is 2-(3,4-dichlorophenoxy)-5-ethylthio-3-pyridinecarbonitrile.

68. The composition of claim 61 wherein the compound is 6-(3,4-dichlorophenoxy)-3-isopropylthio-2-pyridinecarbonitrile.

69. The composition of claim 61 wherein the compound is 3-(3,4-dichlorophenoxy)-6-isopropylthio-2-pyridinecarbonitrile.

70. The composition of claim 61 wherein the compound is 6-(3,4-dichlorophenoxy)-3-(sec-butylthio)-2-pyridinecarbonitrile.

71. The composition of claim 61 wherein the compound is 3-(3,4-dichlorophenoxy)-6-(sec-butylthio)-2-pyridinecarbonitrile.

72. The composition of claim 61 wherein the compound is 6-(3,4-dichlorophenoxy)-3-propylthio-2-pyridinecarbonitrile.

* * * * *

UNITED STATES PATENT AND TRADEMARK OFFICE
CERTIFICATE OF CORRECTION

PATENT NO. : 4,558,134

DATED : December 10, 1985

INVENTOR(S) : Yulan C. Tong

It is certified that error appears in the above-identified patent and that said Letters Patent is hereby corrected as shown below:

Column 3, line 45, "5-(phenoxy-2-hydroxy" should read -- 5-(phenoxy)-2-hydroxy --.

Column 6, line 30, "the reaction temperature was stirred" should read -- the reaction mixture was stirred --.

Column 8, line 48, Example 19, "pyridinecarbontrile," should read -- pyridinecarbonitrile,--.

Column 9, Table 1, line 10, Compound Example Number 8, "2-$CH_3C_2S$;" should read -- 2-$CH_3CH_2S$; --.

Column 9, Table 1, line 27, Compound Example Number 15, "6-$CH_3(CH_2)_2C_2S$" should read -- 6-$CH_3(CH_2)_2CH_2S$ --.

Column 12, line 50, "2-hydroxy-b" should read -- 2-hydroxy- --.

Column 23, line 16, "in tests such as" should read -- in texts such as --.

Signed and Sealed this

Twenty-sixth Day of August 1986

[SEAL]

Attest:

DONALD J. QUIGG

Attesting Officer

Commissioner of Patents and Trademarks